United States Patent
Miyagawa et al.

[11] Patent Number: 5,755,707
[45] Date of Patent: May 26, 1998

[54] VASCULAR DILATING CATHETER

[75] Inventors: Katsuya Miyagawa; Shu Kurashima; Nozomu Fujita, all of Osaka, Japan

[73] Assignee: Nissho Corporation, Japan

[21] Appl. No.: 688,331

[22] Filed: Jul. 30, 1996

[30] Foreign Application Priority Data

Aug. 4, 1995 [JP] Japan .................. 7-199386

[51] Int. Cl.$^6$ .................................. A61M 29/00
[52] U.S. Cl. ............................ 604/96; 606/194
[58] Field of Search ............... 604/96–102; 606/192, 606/194

[56] References Cited

U.S. PATENT DOCUMENTS

| | | | |
|---|---|---|---|
| 4,195,637 | 4/1980 | Gruntzig et al. | 128/348 |
| 4,323,071 | 4/1982 | Simpson et al. | 128/343 |
| 4,637,396 | 1/1987 | Cook | 604/102 |
| 4,646,742 | 3/1987 | Packard et al. | 128/344 |
| 4,775,371 | 10/1988 | Mueller, Jr. | 604/280 |
| 5,049,132 | 9/1991 | Shaffer et al. | 604/101 |
| 5,100,385 | 3/1992 | Bromander | 604/99 |
| 5,158,548 | 10/1992 | Lau et al. | 604/96 |
| 5,250,069 | 10/1993 | Nobuyoshi et al. | 606/192 |
| 5,342,305 | 8/1994 | Shonk | 604/101 |
| 5,364,357 | 11/1994 | Aase | 604/96 |
| 5,397,307 | 3/1995 | Goodin | 604/96 |
| 5,423,754 | 6/1995 | Cornelius et al. | 604/103 |
| 5,549,551 | 8/1996 | Peacock, III et al. | 604/96 |

FOREIGN PATENT DOCUMENTS

| | | |
|---|---|---|
| 0274129 | 7/1988 | European Pat. Off. . |
| 0339093 | 11/1989 | European Pat. Off. . |
| WO 88/07389 | 10/1988 | WIPO .................. 606/192 |

*Primary Examiner*—Corrine M. McDermott
*Assistant Examiner*—Deborah Blyveis
*Attorney, Agent, or Firm*—Leydig, Voit & Mayer, Ltd.

[57] ABSTRACT

A vascular dilating catheter comprising an outer tube, an inner tube and a connector, wherein said connector comprises an inlet for injecting a balloon distending solution and an inlet for insertion of a guidewire into the inner tube; the inner tube is inserted into the outer tube; and the outer tube having flexibility at a distal end side and rigidity at a proximal end side is provided with a balloon at the distal end portion thereof, the outer tube being adhered to the inner tube at the position enclosed by the balloon, and the outer tube having, between the proximal end of the balloon and the site of adhesion to the inner tube, a through-hole which connects the inner cavity of the balloon and a circular lumen formed as a gap between the outer tube and the inner tube. According to the catheter of the present invention, various forces applied to the proximal end of the catheter can be directly and positively transmitted to the distal end portion of the catheter. In addition, the distal end portion of the catheter has a suitable bending strength, and the catheter of the present invention is devoid of bending or twisting of the balloon, or snapping of the distal end portion.

16 Claims, 2 Drawing Sheets

VASCULAR DILATING CATHETER

FIELD OF THE INVENTION present invention relates to a vascular dilating catheter to be used for percutaneous transluminal coronary angioplasty (PTCA). More particularly, the present invention relates to an over-the-wire type vascular dilating catheter for PCTA, which permits easier transmission of a pushing force (a force applied by an operator to push an outer tube of a catheter at a labor-assistant end of the catheter) from the proximal end of the catheter to the distal end thereof than in conventional catheters. The vascular dilating catheter of the present invention can be used in percutaneous transluminal angioplasty (PTA) as well.

BACKGROUND OF THE INVENTION

There have been heretofore known, as vascular dilating catheters, an over-the-wire type vascular dilating catheter (U.S. Pat. No. 4,323,071) and an on-the-wire type vascular dilating catheter (U.S. Pat. No. 4,195,637). An on-the-wire type vascular dilating catheter itself has rigidity imparted by the use of a wire or a core wire, and the catheter also functions as a guidewire, so that the use of this type of catheter is inferior to a guidewire method, wherein a vascular dilating catheter is guided to an affected part along a guidewire having a flexible end portion and varying hardness in the lengthwise direction of the guidewire, in the ability to deliver the catheter to the affected part, and has been used for only a limited range of treatments, such as simultaneous multiple-site treatments. It is also defective in that the catheter cannot be replaced, since the catheter itself has a rigidity.

On the other hand, an over-the-wire type vascular dilating catheter has a double tube structure comprising a guidewire lumen and a lumen for balloon distending solution, and has been increasingly used in the prevailing guidewire method. An over-the-wire type vascular dilating catheter permits the catheter to reach an affected part located at a very complicated part in the body, with the help of superior torque transmission and torque following performance of the guidewire, so that it has been frequently used for coronary angioplasty and the like, wherein the success of the surgical operation depends on whether or not the catheter can reach the affected part. In a treatment using a catheter, it often happens that the size of the catheter need to be changed. According to the guidewire method, such exchange of the catheter can be manipulated easily, because, if a guidewire has been inserted through to the affected part, a new catheter can be also passed up to the affected part by only following the guidewire.

The conventional over-the-wire type vascular dilating catheters include those of a structure wherein the proximal end and the distal end of a balloon are attached to the distal ends of an outer tube and an inner tube, respectively, and those of a structure wherein a distensible member is formed as a part of the outer tube and connected to the inner tube at an end portion thereof. Since the inner and outer tubes are connected by a flexible balloon, the pushing force from the proximal end of the catheter, which is transmitted through the outer tube of the catheter, is weakened at the balloon part and is not transmitted to the end portion of the catheter with certainty. When the tip of the catheter is pushed back toward the operator, the inner tube is thrusted back into the outer tube to cause bending of the inner tube, which in turn causes bending of the balloon or twisting of the balloon by the application of a rotation torque. In addition, since the balloon and the distal end portion of the catheter are supported by a relatively thin inner tube alone, the strength against bending of said region is defectively small.

It is therefore an object of the present invention to provide a vascular dilating catheter capable of positively transmitting the pushing force applied at the labor-assistant end to the distal end portion of the catheter, which is devoid of bending or twisting of the balloon, or snapping of the distal end portion of the catheter.

SUMMARY OF THE INVENTION

The vascular dilating catheter of the present invention comprises an outer tube and an inner tube inserted in said outer tube. The outer tube has flexibility at the distal end side and rigidity at the proximal end side. A balloon is formed at the distal end portion of the outer tube and the outer tube is adhered to the inner tube at a position enclosed by the balloon. The outer tube has, between the proximal end of the balloon and the site of adhesion to the inner tube, a through-hole which connects the inner cavity of the balloon and a circular lumen formed as a gap between the outer tube and the inner tube. The catheter further comprises, at the proximal end thereof, a connector having an inlet to feed a solution to inflate the balloon and an inlet for the insertion of a guidewire into the inner tube.

The outer tube may be formed only up to the connection with the inner tube, which connection being enclosed by the balloon. Then, the catheter may have only the inner tube thereafter to the tip.

The connection between the connector and the outer tube may be reinforced with a bending-preventive tube, and an X-ray impermeable mark may be formed on the outer tube at a position enclosed by the balloon.

DETAILED DESCRIPTION OF THE INVENTION

The embodiment of the present invention is detailedly described in the following based on the drawings.

Figure 1:
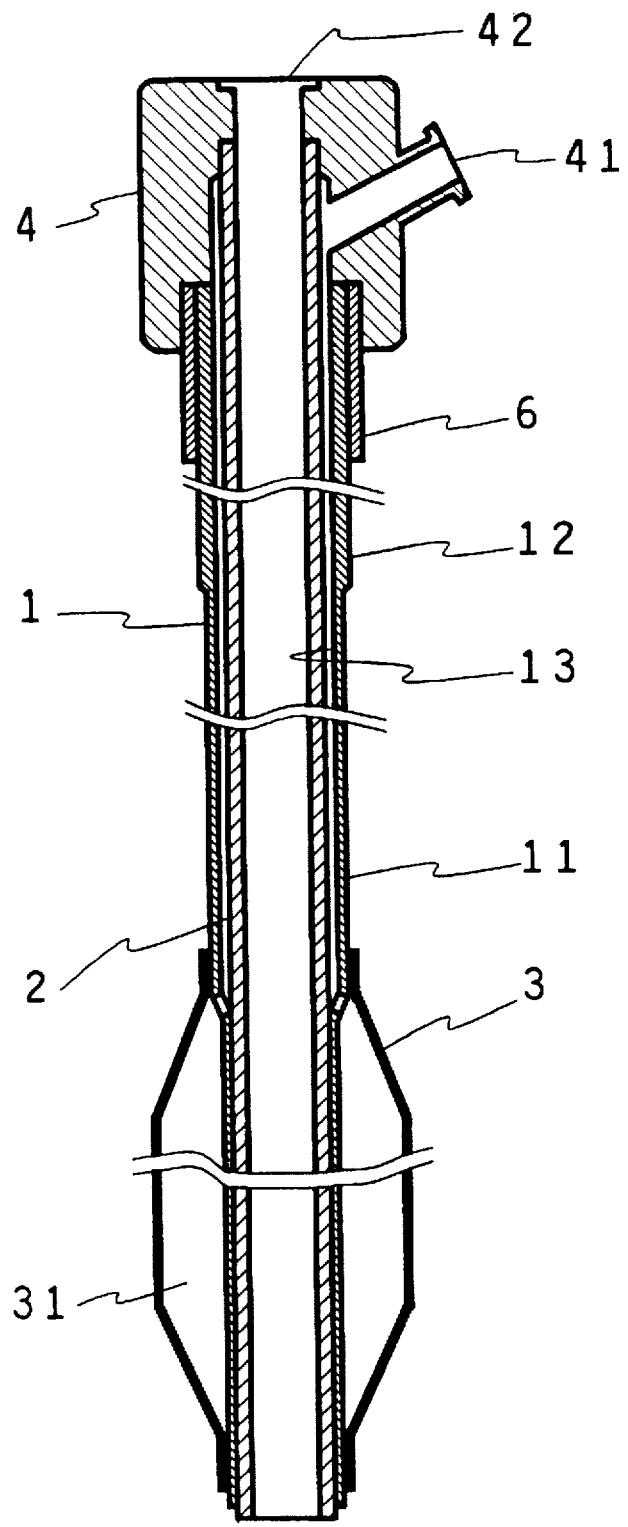
FIG. 1 is a lengthwise cross section of one embodiment of the present invention.
Figure 2:
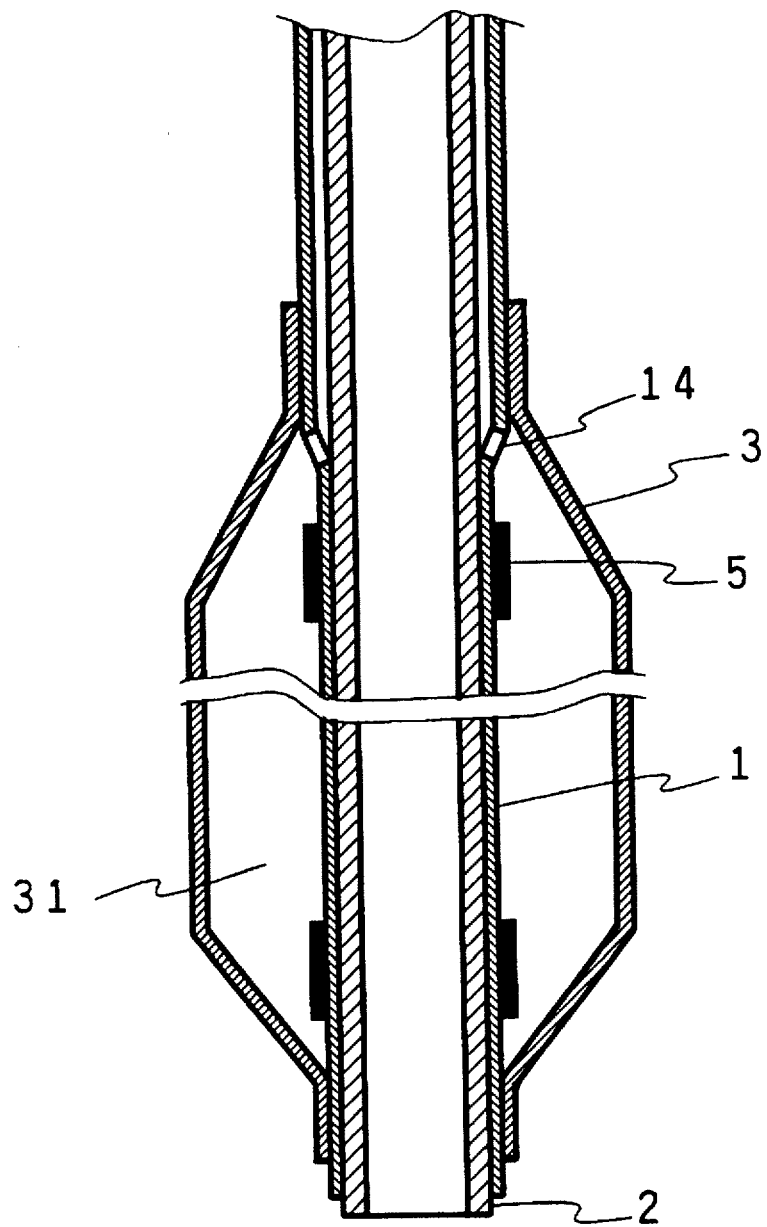
FIG. 2 is a partially enlarged cross section of a distal end portion including the balloon shown in FIG. 1.

FIG. 1 is a lengthwise cross section of one embodiment of the present invention, and FIG. 2 is a partially enlarged cross section of an end portion including the balloon shown in FIG. 1.

As shown in FIG. 1, the vascular dilating catheter of the present invention has an outer tube 1 having a balloon 3 at the distal end portion thereof, and an inner tube 2 inserted in this outer tube 1. A connector 4 is installed at the proximal end and the outer tube 1 is adhered to the outer wall of the inner tube 2 at the position enclosed by the balloon 3. The outer tube 1 consists of a flexible distal end portion 11 and a rigid proximal end portion 12. The connector 4 is a tubular member having an inlet 41 formed for injecting a balloon distending solution and an inlet 42 for inserting a guidewire. The balloon 3 is inflated with a balloon distending solution injected from the inlet 41 for injecting a balloon distending solution which passes through a circular lumen 13 and a side hole 14.

The outer tube 1 is formed from a flexible resin such as olefine resins (e.g., ethylene-vinyl acetate copolymer, polyethylene, polypropylene and ethylene-propylene copolymer), fluororesins (e.g., ethylene polytetrafluoride and ethylene tetrafluoride-propylene hexafluoride copolymer), polyester, polyvinyl chloride, polyurethane, polyethylene terephthalate (PET) and polyamide, and has a balloon 3 at the distal end side thereof. The proximal end thereof is connected to the connector 4 liquid-tightly, and is connected to the inlet 41 for injecting a balloon distending solution. The flexible end portion 11 has smaller inner diameter and thickness than the rigid proximal end portion 12. Therefore, the rigid portion 12 has a suitable rigidity to stand bending, while the flexible portion 11 has a suitable flexibility permitting easy and smooth guiding of the catheter along the guidewire (not shown) to the affected part. The length of the flexible portion 11 is not particularly limited, but is generally 50–350 mm which is determined according to the length of the catheter to be inserted.

An inner tube 2 having a smaller outer diameter than the inner diameter of the outer tube 1 is inserted in the outer tube 1. Therefore, the gap between the outer tube 1 and the inner tube 2 forms the inlet 41 for injecting a balloon distending solution, which inlet being formed in the connector 4, and circular lumen 13 to pass liquids. The flexible portion 11 of the outer tube 1 is liquid-tightly adhered to the outer wall of the inner tube 2 at the position enclosed by the balloon 3. Therefore, this circular lumen 13 advances into the inside of a space 31 between the balloon 3 and the outer tube 1, and has a closed end there. A side hole 14 is formed at the position of the outer tube 1 which is enclosed by the balloon 3 and is at the proximal end side from the adhered portion on the inner tube 2, and the circular lumen 13 passes liquid through this side hole 14 and into the space 31 in the balloon 3. The outer tube 1 may have an X-ray impermeable mark 5 as necessary on the portion enclosed by the balloon 3 for an easy recognition of the position of the inserted catheter. The effective length of the catheter is generally about 1350 mm, and the length from the tip of the catheter to the border line between the flexible portion 11 and the rigid portion 12 is preferably about 150 mm.

The inner tube 2 is formed from a flexible resin like the outer tube 1, and has an outer diameter which is smaller than the inner diameter of the outer tube 1. The circular lumen 13 is formed in the space of the inner tube 2 and the outer tube 1. The proximal end of the inner tube 2 is liquid-tightly connected to the guidewire insertion inlet 42 in the connector 4, such that a balloon distending solution injected from the inlet 41 does not leak out.

The connector 4 is a tubular member liquid-tightly connected to the outer tube 1 and the proximal end of the inner tube 2, and is generally formed from a flexible resin such as polyethylene, polypropylene, polyester, polyvinyl chloride, ABS resin and polycarbonate. The connection between the connector 4 and the outer tube 1 may be reinforced with a bending-preventive tube 6, so that the catheter will not bend near the hand of an operator during a catheter guiding operation.

The balloon 3 is generally a thin film having a thickness of from 0.001 mm to 0.1 mm, and adhered to the outer wall of the outer tube 1 with an adhesive or by thermal bonding. The balloon 3 is formed from a material having suitable toughness and strength. The material of the balloon 3 may be various known thermoplastic resins, and is not particularly limited. For example, a material prepared by mixing an ethylene-butyrene-styrene block copolymer and a low molecular weight polystyrene and adding polypropylene as necessary, polyvinyl chloride, polyester, thermoplastic rubber, silicone-polycarbonate copolymer, ethylene-vinyl acetate copolymer, polyethylene terephthalate, polyamide and the like may be used.

The balloon and the surrounding portion are preferably configurated as follows.
(1) The total length of the distensible portion of the balloon, namely, from the proximal end to the distal end of the balloon, is preferably from 10 mm to 50 mm.
(2) The outer diameter of the tubular portion of the balloon upon inflation is 1–30 mm.
(3) The outer and inner tubes are adhered to each other throughout the region from the vicinity of the proximal end of the balloon [see (4) below] to the distal end of the catheter.
(4) The starting point of adhesion between the outer tube and inner tube is preferably 0.5 mm–10 mm apart from the proximal end of the balloon, rather than from the same position with the proximal end of the balloon.
(5) In addition to (4) above, the starting point of the adhesion between the outer tube and inner tube is preferably somewhere between the vicinity of the proximal end of the balloon and the middle (50% of the total length) of the balloon.

In the vascular dilating catheter of the present invention, the force or displacement applied to the outer tube is directly transmitted to the inner tube in both lengthwise direction and twisting direction. That is, various forces applied to the proximal end of the catheter, such as a pushing force for insertion and advancing of the catheter and twisting force for rotation of the catheter, are directly and positively transmitted to the distal end portion of the catheter without being absorbed by intervening members such as a balloon. In addition, the distal end portion of the catheter has a suitable bending strength by the reinforcement with the outer tube.

Speaking from the aspect of the balloon, it is attached to the outer tube at both ends, and is free from the function of an intervening member to transmit the force from the outer tube to the inner tube. Accordingly, the balloon is free from the force applied to the outer tube or relative dislocation between the outer tube and inner tube, thus obviating conventionally problematic sagging and wrinkles on the balloon.

What is more, while the balloon is mounted on the outer tube over the entire length of from the proximal end to the distal end of the balloon, since the outer tube has a smaller outer diameter at the position where it is adhered to the inner tube, the balloon, when deflated, does not protrude appreciably from the maximum outer diameter of the outer tube, so that the catheter can move smoothly in the blood vessel.

What is claimed is:

1. A vascular dilating catheter comprising an outer tube with a proximal end and a distal end, an inner tube with a proximal end and a distal end, and a connector, wherein said connector is secured to the respective proximal ends of the outer and inner tubes to provide sealed fluid communication with the outer tube and wherein said connector comprises an inlet for injecting a balloon distending solution and an inlet for insertion of a guidewire into the inner tube the inner tube is inserted into said outer tube such that the inner and outer tubes are concentrically positioned to form a circular lumen therebetween; and the outer tube having flexibility at the distal end and rigidity at the proximal end, and is provided with a balloon at the distal end portion thereof, the outer tube being adhered to the inner tube by a fixed circumferential contact at a position enclosed by the balloon, and the outer tube having, between the proximal end of the balloon and the site of adhesion to the inner tube, a through-hole which connects the inner cavity of the balloon and the circular lumen.

2. The vascular dilating catheter of claim 1, wherein the balloon has a distensible portion which has a total length of about 10 mm–50 mm.

3. The vascular dilating catheter of claim 1, wherein the balloon has a portion which becomes tubular upon inflation, and the outer diameter of the tubular portion is from 1 mm to 30 mm.

4. The vascular dilating catheter of claim 1, wherein the outer tube extends up to a tip of the catheter, and the outer tube is adhered to the inner tube from a position enclosed by a balloon to the tip of the catheter.

5. The vascular dilating catheter of claim 1, wherein the starting point of adhesion of the outer tube to the inner tube is 0.5 mm–10 mm apart from th e proximal end of the balloon.

6. The vascular dilating catheter of claim 1, wherein the connection between the connector and the outer tube is reinforced with a bending-preventive tube.

7. The vascular dilating catheter of claim 1, wherein the outer tube has an X-ray impermeable marker on the portion enclosed by the balloon.

8. The vascular dilating catheter of claim 1, wherein the fixed circumferential contact between the inner and outer tubes extends substantially along an axial length of the balloon, beginning distally adjacent to a proximate end of the balloon.

9. The vascular dilating catheter of claim 1, wherein said fixed circumferential contact between the inner and outer tubes extends to a distal tip of the catheter.

10. A vascular dilating catheter comprising: an outer tube with opposite proximal and distal ends; an inner tube with opposite proximal and distal ends; a balloon secured to a distal portion of the outer tube; and a connector secured to the proximal ends of the tubes for communication therewith; the inner tube being concentrically positioned within the outer tube to form a circular lumen therebetween, the inner tube and the outer tube being adhered together by a fixed circumferential contact near the distal ends, the inner tube having a hole extending therethrough at a position proximal to the circumferential contact to permit fluid communication between the lumen and an interior of the balloon.

11. The catheter according to claim 10, wherein said connector includes an opening providing access for insertion of a guidewire into said inner tube and an opening for injecting a solution into said lumen.

12. The catheter according to claim 10, wherein said inner and outer tubes extend up to said distal tip of said catheter.

13. The catheter according to claim 10, wherein said fixed circumferential contact extends substantially along an axial length of said balloon.

14. The catheter according to claim 10, wherein the outer tube has flexibility at a distal portion and rigidity at a proximal portion thereof.

15. The catheter according to claim 10, wherein said balloon has a proximal end secured around said outer tube proximally to said hole and a distal end secured around said outer tube near said distal tip.

16. The catheter according to claim 10, wherein said fixed circumferential contact between the inner and outer tubes extends distally beyond the distal end of the balloon.

* * * * *

UNITED STATES PATENT AND TRADEMARK OFFICE
CERTIFICATE OF CORRECTION

PATENT NO. : 5,755,707
DATED : May 26, 1998
INVENTOR(S) : MIYAGAWA et al.

It is certified that error appears in the above-identified patent and that said Letters Patent is hereby corrected as shown below:

In Column 1, line 5: "present invention" should read --The present invention--.

IN THE CLAIMS:

In Claim 5, Column 5, line 11: "th e" should read --the--.
In Claim 10, Column 6, line 3: "therebetween, the" should read -- therebetween; the--.

Signed and Sealed this

Twenty-seventh Day of October, 1998

*Attest:*

BRUCE LEHMAN

*Attesting Officer*  *Commissioner of Patents and Trademarks*